(12) United States Patent
Auckenthaler

(10) Patent No.: US 9,341,593 B2
(45) Date of Patent: May 17, 2016

(54) CONTROL METHOD AND DEVICE FOR OXYGEN PUMP CELLS OF SENSORS IN INTERNAL COMBUSTION ENGINES OR EXHAUST GAS AFTER TREATMENT SYSTEMS OF SUCH ENGINES

(75) Inventor: Theophil Auckenthaler, St. Gallen (CH)

(73) Assignee: FPT MOTORENFORSCHUNG AG, Arbon (CH)

( * ) Notice: Subject to any disclaimer, the term of this patent is extended or adjusted under 35 U.S.C. 154(b) by 952 days.

(21) Appl. No.: 13/261,334

(22) PCT Filed: Dec. 22, 2010

(86) PCT No.: PCT/EP2010/070464
§ 371 (c)(1),
(2), (4) Date: Jun. 22, 2012

(87) PCT Pub. No.: WO2011/076832
PCT Pub. Date: Jun. 30, 2011

(65) Prior Publication Data
US 2012/0288376 A1 Nov. 15, 2012

(30) Foreign Application Priority Data
Dec. 23, 2009 (EP) .................................. 09180650

(51) Int. Cl.
*G01N 27/419* (2006.01)
*G01N 27/406* (2006.01)

(52) U.S. Cl.
CPC .......... *G01N 27/419* (2013.01); *G01N 27/4065* (2013.01)

(58) Field of Classification Search
CPC .. G01N 27/406–27/41; G01N 27/417–27/419; F02D 41/1438–41/1496; F02D 41/22–41/222; F01N 11/007; G01M 15/10–15/108; B01D 53/32–53/326; Y02T 10/47
See application file for complete search history.

(56) References Cited

U.S. PATENT DOCUMENTS 4,707,241 A    11/1987   Nakagawa

FOREIGN PATENT DOCUMENTS

| JP | S61204558 | 9/1986 |
|----|-----------|--------|
| JP | H07166938 | 6/1995 |
| JP | H07180585 | 7/1995 |
| JP | H09113481 | 5/1997 |
| JP | H1114593  | 1/1999 |
| JP | H11108887 | 4/1999 |
| JP | H11211693 | 8/1999 |
| JP | H11218516 | 8/1999 |
| JP | 2001133429 | 5/2001 |
| JP | 2001343357 | 12/2001 |
| JP | 2003050227 | 2/2003 |
| JP | 2005030358 | 2/2005 |
| JP | 2005351788 | 12/2005 |
| JP | 2007003515 | 1/2007 |
| JP | 2007198901 | 8/2007 |
| JP | 2008075571 | 4/2008 |
| JP | 2009287439 | 12/2009 |

*Primary Examiner* — J. Christopher Ball
(74) *Attorney, Agent, or Firm* — Stetina Brunda Garred & Brucker

(57) ABSTRACT

It is described a method for controlling an oxygen pump cell of a sensor in an internal combustion engine or in the exhaust gas after treatment system of such an engine, comprising the step of adding, to a feedback control of the current in the pump cell, a further feed-forward control path estimating an expected oxygen pump current on the basis of characteristics of the exhaust gas composition calculated from engine operation data.

7 Claims, 6 Drawing Sheets

CONTROL METHOD AND DEVICE FOR OXYGEN PUMP CELLS OF SENSORS IN INTERNAL COMBUSTION ENGINES OR EXHAUST GAS AFTER TREATMENT SYSTEMS OF SUCH ENGINES

FIELD OF THE INVENTION

The present invention relates to an improved control method and device for Oxygen pump cells of sensors in internal combustion engines or exhaust gas after treatment systems of such engines.

DESCRIPTION OF THE PRIOR ART

Combustion engines which have to comply with current and future emission legislations make use of an after-treatment system and/or of an exhaust gas recirculation (EGR) system in order to reduce the NOx emissions below the limits imposed by the law. Both types of systems rely on solid-state oxygen, NOx, and lambda sensors. These sensors contain electrochemical pumps, where oxygen ions are pumped through a solid-state electrolyte cell.

As shown in FIG. 1, a Lambda sensor contains a reference cavity 1 with air and a measurement cavity 2 with exhaust gas. The exhaust gas enters the measurement cavity through a diffusion barrier 3. A pump cell 4, using a solid-state electrolyte, is present between the cavity 2 and the exhaust gas side. Through the pump cell 4, oxygen is pumped electrochemically out of the cell, or into the cell for gasoline systems.

A potentiometric lambda sensor cell 5 is present between the reference cavity 1 and the measurement cavity 2. The pump current of the pump cell 4, which is equivalent to the oxygen ion current, is controlled such that the electrochemical potential 6, obtained from the potentiometric lambda sensor cell 5, between the measurement cavity and the reference cavity is maintained at a constant level. Usually this level corresponds to an oxygen concentration in the measurement cavity close to zero. The pump current of the pump cell strongly correlates with the oxygen concentration in the exhaust gas. Therefore, the oxygen concentration can be obtained from the pump current.

As shown in FIG. 2, the structure of an Oxygen sensor is similar to that of the Lambda sensor of FIG. 1. The Oxygen sensor does not maintain a constant electrochemical potential 6 between the measurement (2) and the reference (1) cavities, but rather the electrochemical potential 6 ramps up and down between two well-defined levels using constant pump currents in the pump cell 4. The oxygen concentration can then be obtained from the ramping time between the two potential levels.

As shown in FIG. 3, a NOx sensor shows a reference cavity 1 with air, and at least two consecutive measurement cavities with relating electrochemical pumps. The exhaust gas enters the first measurement cavity 8 through a diffusion barrier 9. The first pump cell 10 of the first measurement cavity exhibits a selectivity to oxygen, such that NOx are not affected. Using this pump, oxygen is almost completely removed from the gas in the first cavity 8. The remaining gas containing small amounts of oxygen and the NOx enters the second measurement cavity 11 through a second diffusion barrier 12. The second pump cell 13 is designed such that the pump current is correlated to both the oxygen ion currents from the gas and from dissociated NOx. Hence, the pump current of the second cell 13 strongly correlates with the NOx concentration and can therefore be used for its determination.

All sensing principles described above rely on stable pump current feedback control loops. During transient operation of the engine, the oxygen content may vary very strongly and quickly, which causes heavy disturbances in the control loops and therewith unstable sensor signals. Generally, the sensor signals are not reliable during transient operation, especially in the Diesel environment, where the expected variations of the oxygen concentrations are very significant. In gasoline and natural gas engines, which are generally operated at a constant air/fuel ratio, such variations only occur during fuel cut-off phases.

In the known sensors therefore the reduced reliability during transient phases makes nonlinear filter techniques necessary, which however may significantly slow down and also disturb the sensor response and therefore the bandwidth of the feedback control loops in the engines.

SUMMARY OF THE INVENTION

Therefore it is the main object of the present invention to provide an improved control method and device for Oxygen pump cells of sensors in internal combustion engines or exhaust gas after treatment systems of such engines.

The basic idea of the present invention is to improve the controller of the oxygen pump current in a solid-state electrolyte sensor device by a feed-forward path using process data of the engine.

Preferably there will be used air/fuel ratio, oxygen concentration, NOx concentration, or other characteristics of the exhaust gas calculated from engine operation data to estimate the expected oxygen pump current.

Preferably there will be used physical quantities characterizing the state of the exhaust gas such as temperatures, pressures, humidity, engine speed, fuel quantity, pressure pulsations to anticipate and compensate for potential disturbances and deviations of the expected oxygen pump current.

These and further objects are achieved by means of an improved control method and device for Oxygen pump cells of sensors in internal combustion engines or exhaust gas after treatment systems of such engines, as described in the attached claims, which form an integral part of the present description.

BRIEF DESCRIPTION OF THE DRAWINGS

The invention will become fully clear from the following detailed description, given by way of a mere exemplifying and non limiting example, to be read with reference to the attached drawing figures, wherein.

The same reference numerals and letters in the figures designate the same or functionally equivalent parts.

DETAILED DESCRIPTION OF THE PREFERRED EMBODIMENTS

According to the invention, engine operation data are used in order to improve the performance of the oxygen pump controller. This allows a significant acceleration of the sensor response, which in turn increases the sensor accuracy during transient phases and thus allows the extension of the control loop bandwidth.

The approximate oxygen partial pressure and/or air/fuel ratio (lambda) are critical quantities both for general engine management and for the after-treatment systems. Therefore, this information is always available in an engine control unit. Since these quantities can be directly calculated from the injected fuel and the current amount of oxygen in the cylinder, it is always available prior to influencing a sensor mounted downstream of the engine cylinder outlet. Therefore, this information can be used to pre-adjust the oxygen pump current by means of a feed-forward controller.

With such a setup the feedback controller only needs to level out local disturbances. This in turn allows the use of simple filter algorithms and therewith a significant extension of the control loop bandwidth.

Figure 3:
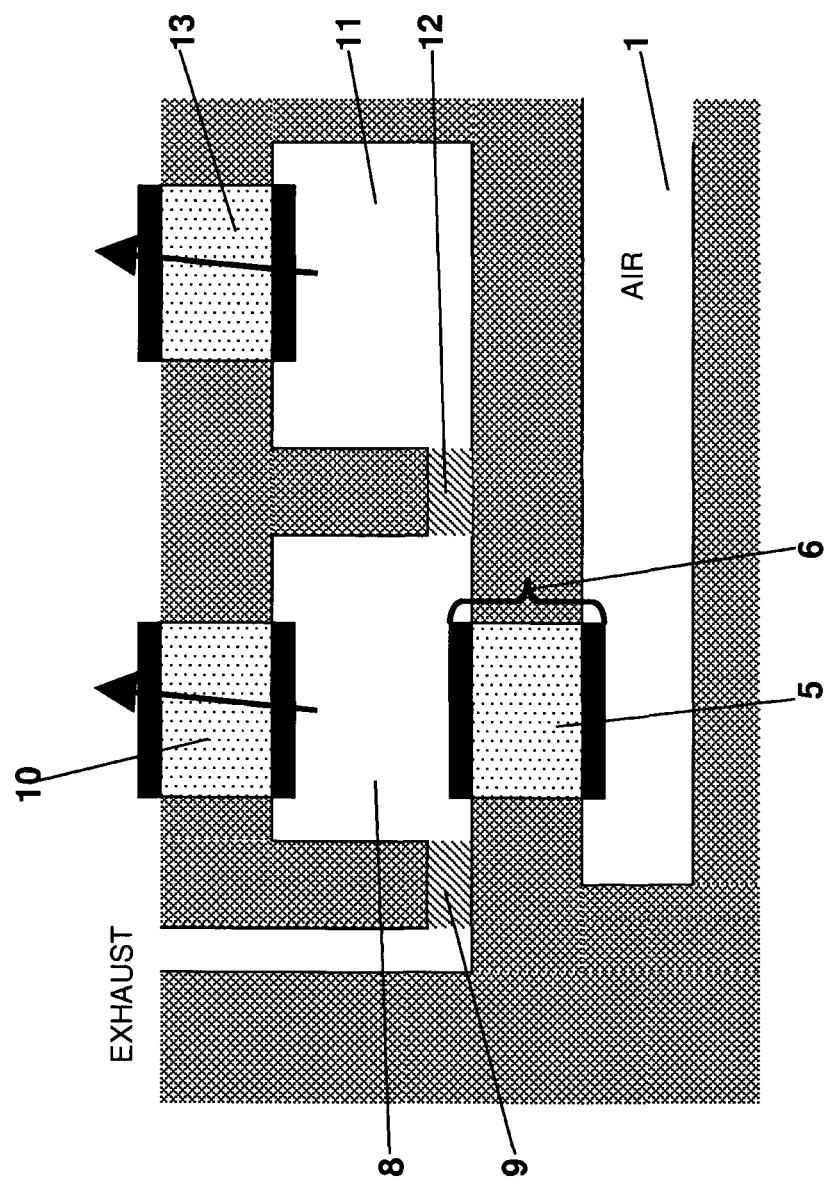
FIG. 3 shows a schematic view of an NOx sensor of known type.
Figure 4:
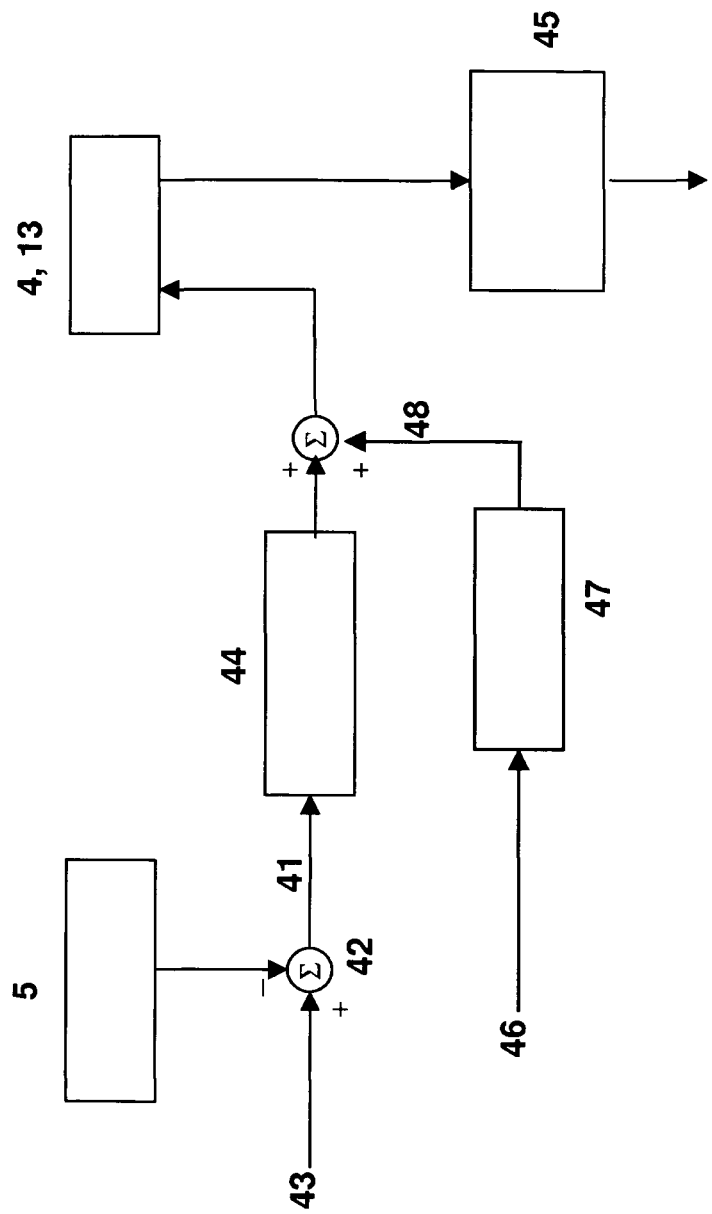
FIG. 4 shows a schematic view of a pump current controller including the additional feed forward path according to the present invention.

With reference to FIG. 4, a known pump current controller comprises determining, through an adder 42, a voltage 41 given by the difference between the output voltage of the potentiometric cell (5 in FIGS. 1, 2, 3) and a reference voltage 43 from a voltage set point. The latter is determined in a way known per se. For example in lambda (λ) and NOx sensors, this voltage is usually around 450 mV, which corresponds to stoichiometry, i.e, the condition where neither surplus oxygen nor surplus reducing agents (CO, H2, HC, etc. . . . ) are present.

Figure 5:
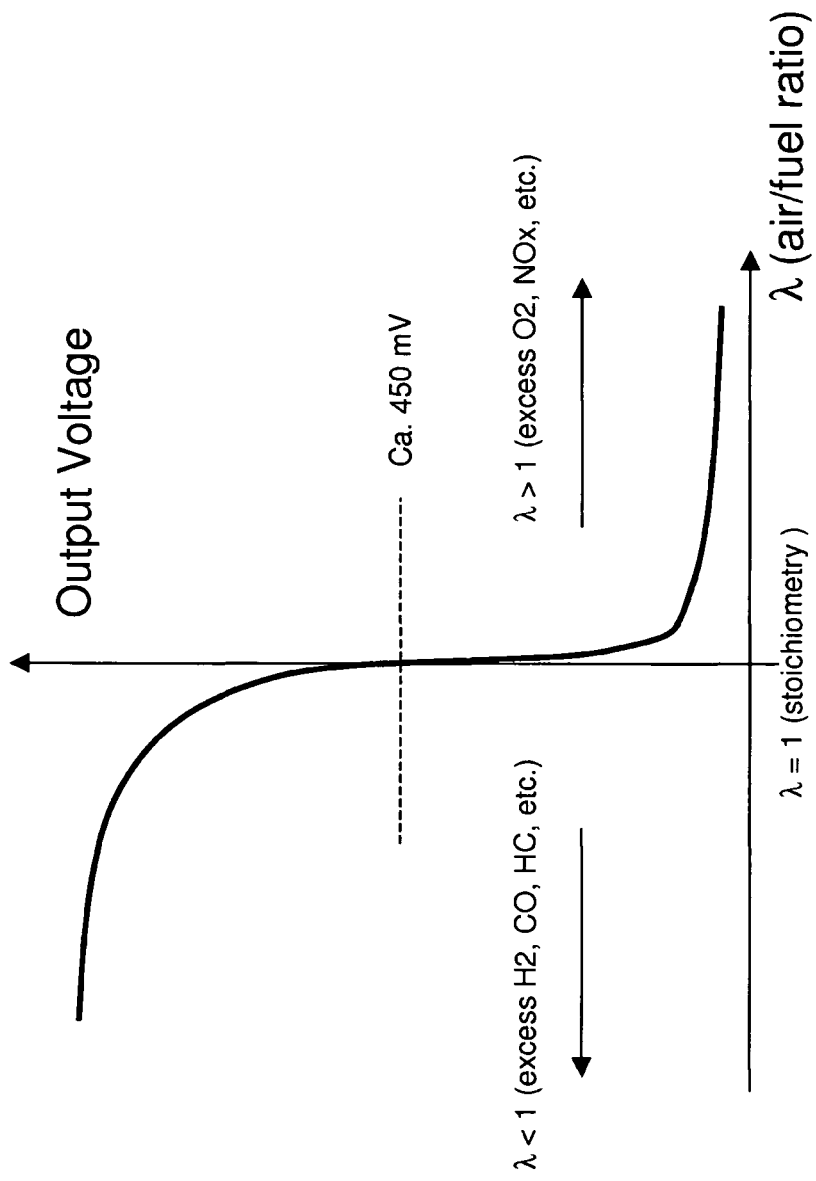
FIG. 5 shows a possible trend of the output voltage of the potentiometric lambda sensor vs. the lambda values.

With reference to FIG. 5, a typical trend of lambda λ (air/fuel ratio) vs. Output voltage in a potentiometric lambda sensor is shown: in the central point we have (450 mV), λ=1 (stoichiometry, where only N2, H2O, CO2, etc. . . . are present); for λ<1 (excess of H2, CO, HC, etc. . . . ), the output voltage increases; for λ>1 (excess of O2, NOx, etc. . . . ) the output voltage decreases.

Figure 1:
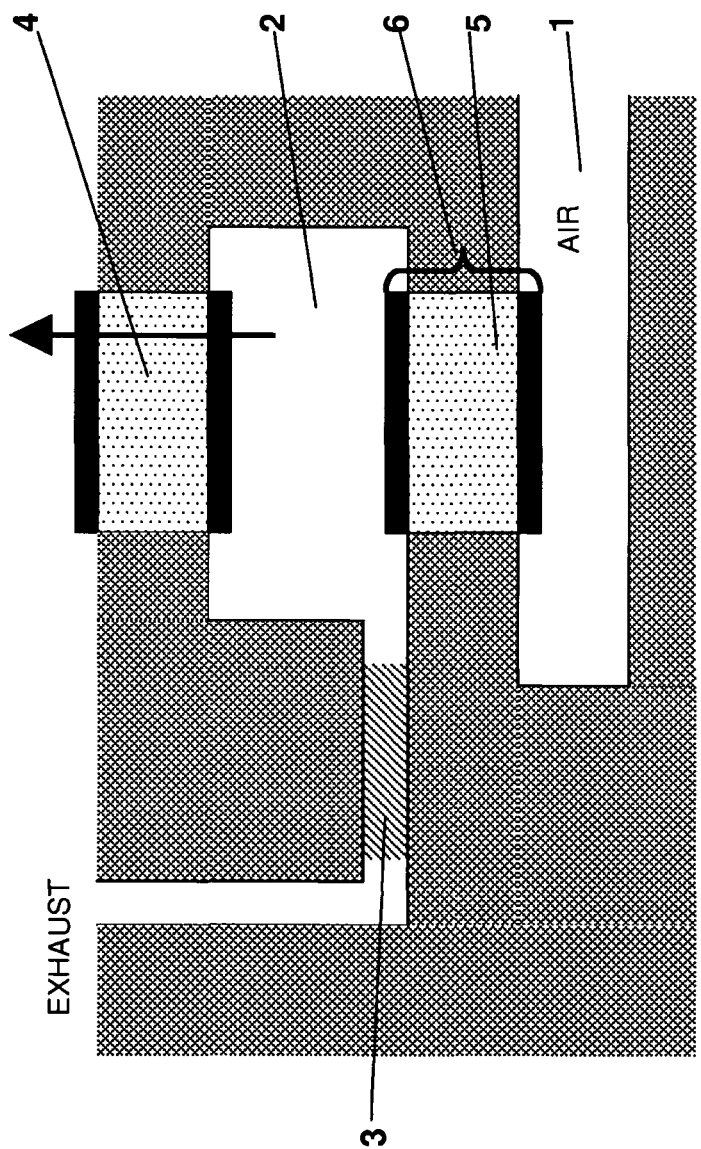
FIG. 1 shows a schematic view of a lambda sensor of known type.
Figure 2:
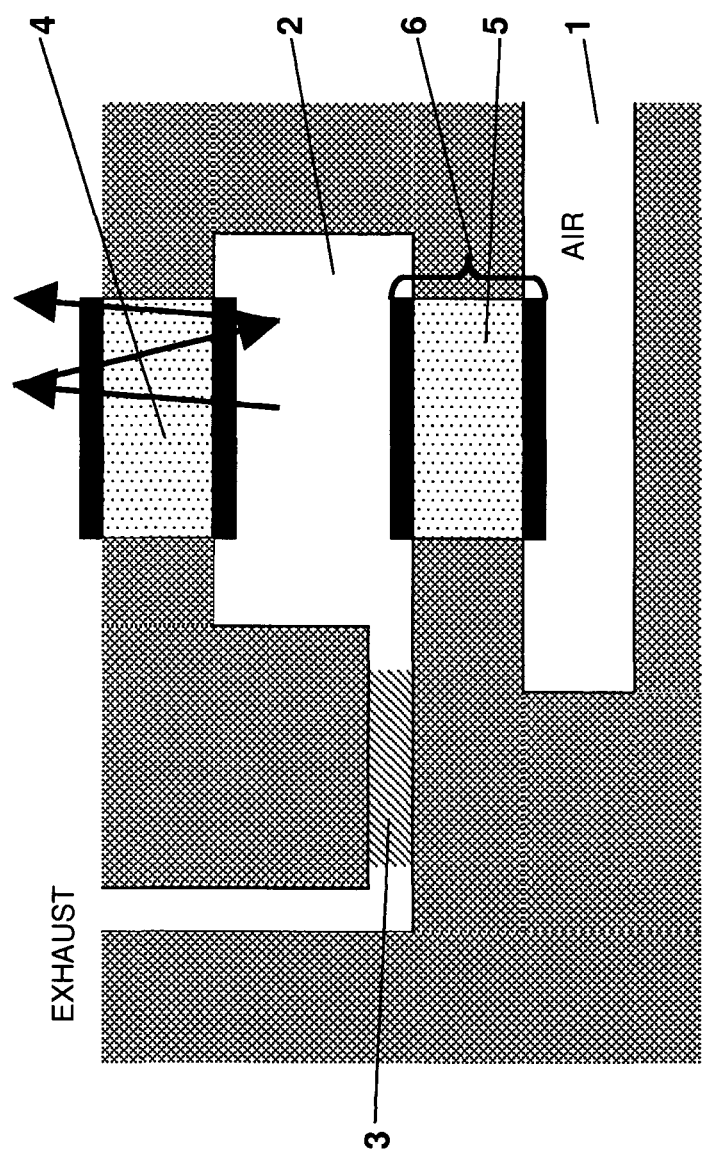
FIG. 2 shows a schematic view of an oxygen sensor of known type.

The voltage 41 is brought to the input of a pump current controller 44 for the current in the pump cell (4 in FIGS. 1,2, and 13 in FIG. 3). The constitution of the pump current controller 44 is known. In the known controllers the output of the current controller 44 is the only contribution given to the pump cell. The current at the output of the pump cell (4, 13 in FIGS. 1, 2, 3) is measured in a measurement block 45 of the known type, as also described above, giving at the output the voltage imposed on the pump cell.

According to the invention, an estimated parameter Lambda 46, coming from the electronic control unit of the vehicle, is brought to the input of a pump current estimator 47, the output 48 of which is used as a feed forward control in addition to the output of the pump current controller 44, contributing to the determination of the desired current and therefore of the voltage in the pump cell.

Figure 6:
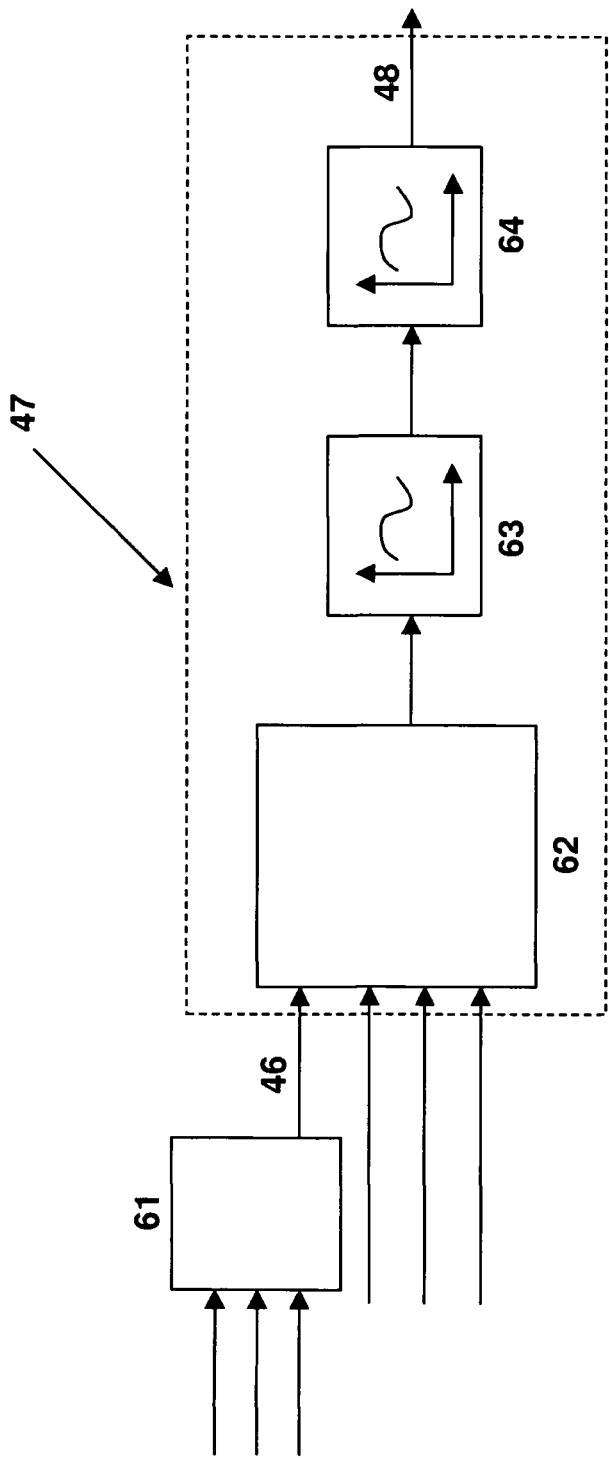
FIG. 6 shows a more detailed schematic view of the additional feed forward path according to the present invention.

With reference to FIG. 6, the parameter Lambda 46 is estimated in a known way in a block 61, for example from input measured values of the fresh air mass entering the cylinder, the injected fuel mass, and the mass of the recirculated exhaust gas at cylinder outlets.

The pump current estimator 47 comprises a block 62 which estimates the transport time delay from the cylinders to the sensor, on the basis of input data, namely the estimated parameter Lambda 46 of air/fuel ratio, and also other input measured values already available of the gas mass flow, for example the oxygen and NOx concentrations, the piping volume, the gas pressure, the gas temperature, humidity, engine speed, fuel quantity, pressure pulsations. The time delay can for example be obtained from the gas mass in the volume between the cylinder outlet and the sensor position and from the gas mass flow by dividing the former by the latter quantity.

The stored gas mass in turn can be calculated from the pressures, the temperatures, and the pipe volumes using the well-known gas equation.

In addition in the pump current estimator 47 there are also available tables of relations between the lambda parameter and the oxygen concentration in the measured gas (block 63), and the oxygen concentration and the pump current (block 64). These relations are pre-loaded and depend on the specific system setup, i.e., both on the engine and the used sensor. Examples of these tables can be found for example in the Bosch Automotive Handbook, $7^{th}$ edition, ISBN 978-0-470-51936-3.

Taking into account the estimated transport time delay, the two curves give at the output 48 the expected values of the relative parameters in blocks 63 and 64, and eventually the pump current at the time, at which it is anticipated to be necessary for stably maintaining the voltage level of the potentiometric cell 5 (FIG. 4).

The pump current estimator is the same for the three kinds of sensors described above. What can be different are the conditions imposed by the sensor, i.e., the resistance of the diffusion barrier. The amount of oxygen, which enters the cavity, has to be pumped away. Hence, the steady state oxygen molecule flow through the barrier equals the oxygen ion current.

According to the invention, the improved control method comprises improving the controller of the oxygen pump current in the solid-state electrolyte sensor device by the feed-forward path using process data of the engine.

Preferably there will be used air/fuel ratio, oxygen concentration, NOx concentration, or other characteristics of the exhaust gas calculated from engine operation data to estimate the expected oxygen pump current.

Preferably there will be used physical quantities characterizing the state of the exhaust gas such as temperatures, pressures, humidity, engine speed, fuel quantity, pressure pulsations to anticipate and compensate for potential disturbances and deviations of the expected oxygen pump current.

The method of the present invention can be advantageously implemented through a program for computer comprising program coding means for the implementation of one or more steps of the method, when this program is running on a computer. Therefore, it is understood that the scope of protection is extended to such a program for computer and in addition to a computer readable means having a recorded message therein, said computer readable means comprising program coding means for the implementation of one or more steps of the method, when this program is run on a computer.

By means of the present invention, a number of advantages are achieved:
  increased bandwidth of pump current controller in solid-electrolyte sensors, such as oxygen, lambda, or NOx sensors;
  faster response of oxygen, lambda, or NOx sensors;
  improved accuracy of oxygen, lambda, or NOx sensors especially during transient operation and fuel cut-offs;
  improved control of exhaust gas condition (lambda, NOx concentration);
  improved control of after-treatment systems (e.g. SCR) and EGR and thus improved control of emissions.

Many changes, modifications, variations and other uses and applications of the subject invention will become apparent to those skilled in the art after considering the specification and the accompanying drawings which disclose preferred embodiments thereof. All such changes, modifications, variations and other uses and applications which do not depart from the spirit and scope of the invention are deemed to be covered by this invention.

Further implementation details will not be described, as the man skilled in the art is able to carry out the invention starting from the teaching of the above description.

The invention claimed is:

1. A method for controlling an oxygen pump cell of a sensor in an internal combustion engine or in the exhaust gas after treatment system of such an engine, the method comprising the step of adding, to a feedback control of the current in the pump cell, a further feed-forward control path estimating an expected oxygen pump current on the basis of characteristics of the exhaust gas calculated from engine operation data.

2. The method according to claim 1, wherein the internal combustion engine has cylinders, and said feed forward control path comprises:
   estimating a transport time delay of the flow of gas from the cylinders to the sensor on the basis of said characteristics of the exhaust gas;
   using said transport time delay to identify said expected oxygen pump current in tables giving the relations between an air/fuel ratio (lambda) parameter and an oxygen concentration, and the oxygen concentration and the expected oxygen pump current.

3. The method according to claim 1 or 2, wherein said characteristics of the exhaust gas comprise calculated values of air/fuel ratio (lambda), and available values of an exhaust gas mass flow, including one or more of oxygen and NOx contributions, piping volume, gas pressure, gas temperature, humidity, engine speed, fuel quantity, pressure pulsations.

4. A system for controlling an oxygen pump cell of a sensor in an internal combustion engine or in the exhaust gas after treatment system of such an engine, the system comprising:
   a feedback control circuit (44) of the current in the pump cell;
   a feed-forward control estimating circuit (47) of an expected oxygen pump current on the basis of characteristics of the exhaust gas calculated from engine operation data.

5. The system according to claim 4, wherein said feed forward control estimating circuit comprises:
   a circuit for estimating a transport time delay of the flow of gas from the cylinders to the sensor on the basis of said characteristics of the exhaust gas;
   a circuit determining said expected oxygen pump current, on the basis of said transport time delay, identifying said expected oxygen pump current in tables giving the relations between an air/fuel ratio (lambda) parameter and an oxygen concentration, and the oxygen concentration and the expected oxygen pump current.

6. The system according to claim 4, wherein said characteristics of the exhaust gas comprise calculated values of air/fuel ratio (lambda), and available values of an exhaust gas mass flow, including one or more of oxygen and NOx contributions, piping volume, gas pressure, gas temperature, humidity, engine speed, fuel quantity, pressure pulsations.

7. An article of manufacture comprising a non-transitory computer readable medium, said computer readable medium tangibly embodying one or more programs of instructions executable to perform a method for controlling an oxygen pump cell of a sensor in an internal combustion engine or in the exhaust gas after treatment system of such an engine, the method comprising the step of adding, to a feedback control of the current in the pump cell, a further feed-forward control path estimating an expected oxygen pump current on the basis of characteristics of the exhaust gas calculated from engine operation data.

* * * * *